United States Patent
Sato et al.

(10) Patent No.: US 11,651,671 B2
(45) Date of Patent: May 16, 2023

(54) MOTION EVALUATION SYSTEM, MOTION EVALUATION DEVICE, AND MOTION EVALUATION METHOD

(71) Applicant: Hitachi, Ltd., Tokyo (JP)

(72) Inventors: Takuto Sato, Tokyo (JP); Takehiro Niikura, Tokyo (JP); Mitsuhiro Okada, Tokyo (JP); Hiroki Ohashi, Tokyo (JP); Takayuki Akiyama, Tokyo (JP); Katsuyuki Nakamura, Tokyo (JP); Mohammad Osamh Adel Al-Naser, Kaiserslautern (DE); Sheraz Ahmed, Kaiserslautern (DE)

(73) Assignee: Hitachi, Ltd., Tokyo (JP)

( * ) Notice: Subject to any disclaimer, the term of this patent is extended or adjusted under 35 U.S.C. 154(b) by 213 days.

(21) Appl. No.: 17/240,337

(22) Filed: Apr. 26, 2021

(65) Prior Publication Data

US 2021/0335114 A1 Oct. 28, 2021

(30) Foreign Application Priority Data

Apr. 27, 2020 (JP) .............................. JP2020-078491

(51) Int. Cl.
G08B 21/04 (2006.01)
(52) U.S. Cl.
CPC .................... *G08B 21/04* (2013.01)
(58) Field of Classification Search
CPC . G08B 21/04; G06F 2218/10; G06F 2218/16; G06F 3/011; A61B 5/1116;

(Continued)

(56) References Cited

U.S. PATENT DOCUMENTS 6,213,922 B1 * 4/2001 Afanasenko ............... A61F 5/01
482/121
8,948,839 B1 * 2/2015 Longinotti-Buitoni .....................
A61B 5/7405
600/382

(Continued)

FOREIGN PATENT DOCUMENTS

JP          8-241256 A     9/1996
JP       2000-99441 A     4/2000

*Primary Examiner* — Curtis J King
(74) *Attorney, Agent, or Firm* — Crowell & Moring LLP

(57) ABSTRACT

To be capable of efficiently transmitting appropriate information on the motion improvement to a person in motion. A motion evaluation system includes a sensor unit, an information processing device, and an information presentation device. The information processing device includes a communication device, a storage device, and an arithmetic device. The arithmetic device acquires motion data acquired by observing a user through the use of a sensor via the communication device, checks the motion data against information about the correctness of motions in the reference information, determines a state of motion of the user, specifies a motion in a state to be improved as an improvement, check the motion data after the motion corresponding to the improvement against information about busy levels of the user to specify a busy level of the user, and outputs, as improvement suggestion information about the improvement, information with different contents at each of multiple times to an information presentation device based on the improvement and a rule predetermined according to each situation of the busy level.

12 Claims, 17 Drawing Sheets

(58) Field of Classification Search
CPC ... A61B 5/1118; A61B 5/1122; A61B 5/1124; A61B 5/4561; A61B 5/7415; A61B 5/742; A61B 5/746; A61B 2503/10; A61B 2503/20; A61B 2505/09; A61B 2562/0219; A61B 5/486

See application file for complete search history.

(56) References Cited

U.S. PATENT DOCUMENTS

| | | | | |
|---|---|---|---|---|
| 10,325,229 | B2* | 6/2019 | Morgenthau | H04W 4/80 |
| 2001/0007845 | A1* | 7/2001 | Afanasenko | A63B 21/4009 |
| | | | | 482/121 |
| 2001/0008404 | A1 | 7/2001 | Naito et al. | |
| 2006/0241521 | A1* | 10/2006 | Cohen | A61B 5/1123 |
| | | | | 600/595 |
| 2010/0241464 | A1* | 9/2010 | Amigo | A61B 5/112 |
| | | | | 705/4 |
| 2010/0241465 | A1* | 9/2010 | Amigo | G16H 50/30 |
| | | | | 705/4 |
| 2012/0265104 | A1* | 10/2012 | Menegon | A61B 5/4809 |
| | | | | 600/595 |
| 2013/0217352 | A1* | 8/2013 | Pan | A61B 5/747 |
| | | | | 340/539.12 |
| 2014/0200415 | A1* | 7/2014 | McCombie | A61B 5/0285 |
| | | | | 600/301 |
| 2014/0318699 | A1* | 10/2014 | Longinotti-Buitoni | H05K 1/038 |
| | | | | 156/247 |
| 2015/0133279 | A1* | 5/2015 | Alessandri | A47C 9/002 |
| | | | | 482/142 |
| 2015/0309563 | A1* | 10/2015 | Connor | A61B 5/1071 |
| | | | | 73/865.4 |
| 2015/0382086 | A1* | 12/2015 | Kim | H04W 4/70 |
| | | | | 340/870.07 |
| 2016/0070958 | A1* | 3/2016 | Whelan | G06T 7/20 |
| | | | | 382/107 |
| 2016/0148481 | A1* | 5/2016 | Althaher | A61B 5/6823 |
| | | | | 340/573.7 |
| 2016/0202755 | A1* | 7/2016 | Connor | G06F 3/011 |
| | | | | 73/865.4 |
| 2016/0310065 | A1* | 10/2016 | Arif | A61B 5/1116 |
| 2016/0338644 | A1* | 11/2016 | Connor | A61B 5/1126 |
| 2017/0046503 | A1* | 2/2017 | Cho | G16H 40/63 |
| 2017/0196513 | A1* | 7/2017 | Longinotti-Buitoni | A61B 5/7405 |
| 2017/0245806 | A1* | 8/2017 | Elhawary | A61B 5/1122 |
| 2017/0344919 | A1* | 11/2017 | Chang | G09B 5/02 |
| 2018/0160940 | A1* | 6/2018 | Kim | A61B 5/1116 |
| 2019/0179286 | A1* | 6/2019 | Horseman | A41D 19/01594 |
| 2019/0283247 | A1* | 9/2019 | Chang | A61B 5/1121 |
| 2019/0343429 | A1* | 11/2019 | Elhawary | A61B 5/6823 |
| 2021/0195732 | A1* | 6/2021 | Longinotti-Buitoni | H05K 3/361 |
| 2022/0287651 | A1* | 9/2022 | Projetti | A61B 5/0033 |

\* cited by examiner

LOAD EVALUATION TABLE

| ANGLE OF BENT ELBOW | LOAD SCORE |
|---|---|
| 0 - 20 DEGREES | 1 |
| 20 - 40 DEGREES | 2 |
| 40 - 100 DEGREES | 3 |
| 100 DEGREES OR MORE | 4 |

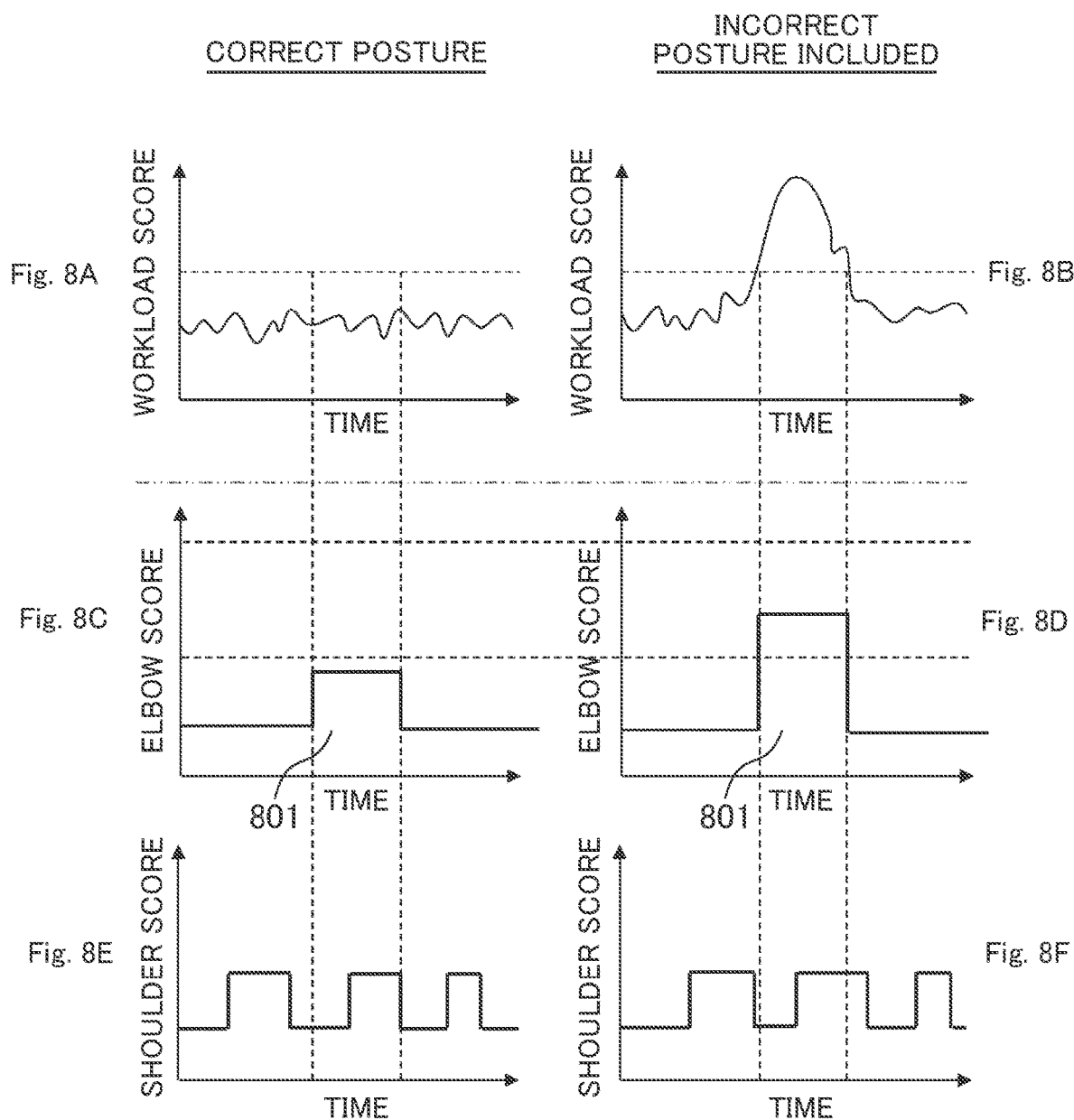

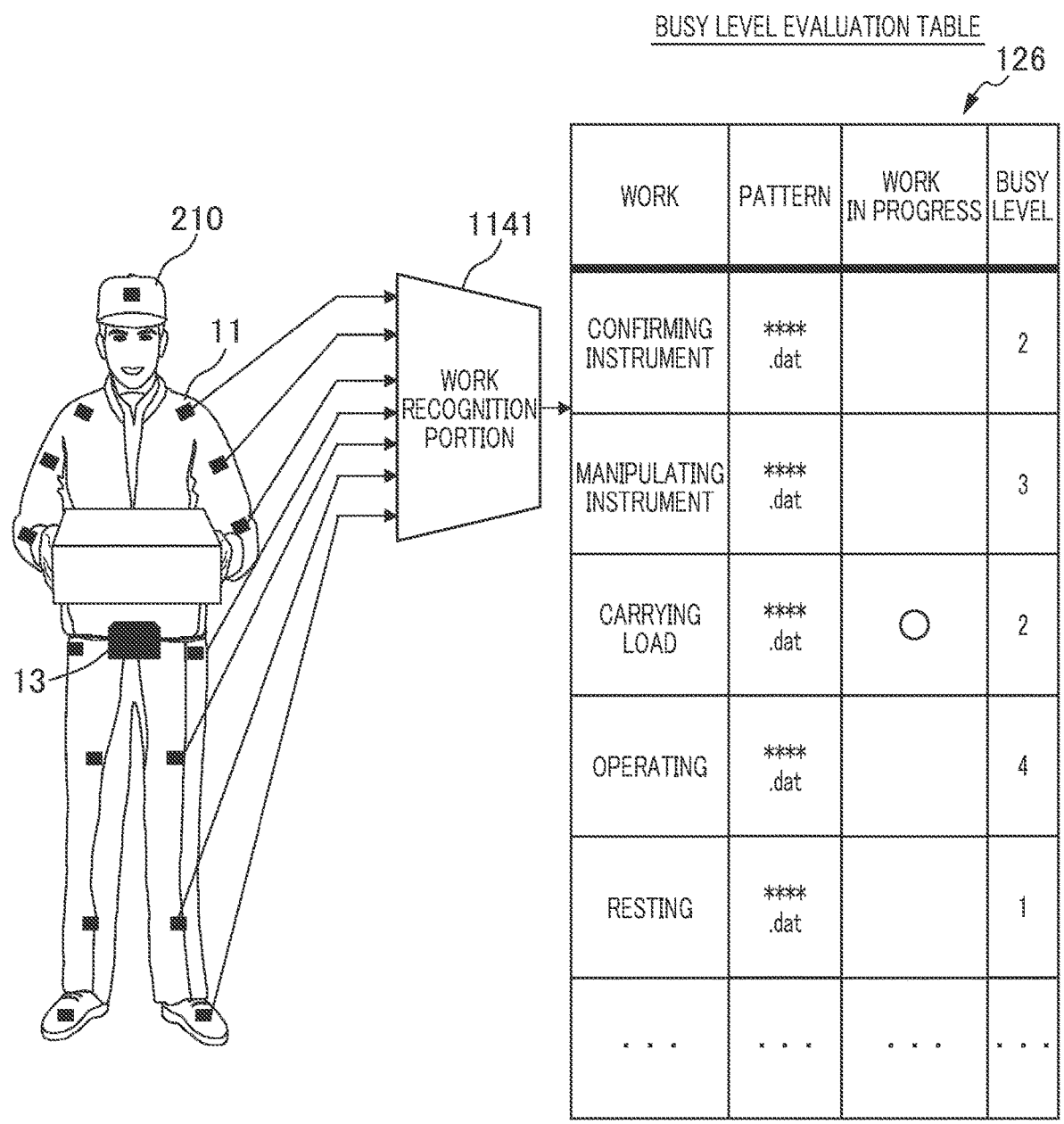

PRESENTATION INFORMATION TABLE

127

| CATEGORY | TYPE | TARGET PART | FEATURE AMOUNT | SKILL LEVEL | CONTENTS | ... |
|---|---|---|---|---|---|---|
| REAL-TIME NOTICE INFORMATION | SOUND | ELBOW | LOAD SCORE 3 OR HIGHER | B+ OR HIGHER | Beep.dat | ... |
| ... | ... | ... | ... | | ... | ... |
| AFTER-THE-FACT NOTICE INFORMATION | TEXT | ELBOW | LOAD SCORE 3 OR HIGHER | B+ OR HIGHER | EXCEPT FOR TENOSYNOVITIS, THE MOTION... | ... |
| ... | ... | ... | ... | | ... | ... |

FIG.17

PERSONAL ATTRIBUTE TABLE

128

| USER ID | AGE | GENDER | ACQUIRED SKILL | SKILL LEVEL | ... |
|---------|-----|--------|----------------|-------------|-----|
| 0001 | 45 | M | OPERATION | A+ | ... |
|  |  |  | ... | ... |  |
| ... | ... | ... | ... | ... | ... |

MOTION EVALUATION SYSTEM, MOTION EVALUATION DEVICE, AND MOTION EVALUATION METHOD

BACKGROUND

Technical Field

The present invention relates to a motion evaluation system, a motion evaluation device, and a motion evaluation method.

Related Art

Various techniques have been proposed to appropriately provide necessary information for those who are in action. For example, the following technologies have been proposed to adjust information based on the type of information, user behavior, or surrounding conditions and present the adjusted information to the user.

One technology includes the information acquisition module and the information amount adjustment module. The information acquisition module acquires information from various sources. The information amount adjustment module adjusts the amount of information to be equal to so that it becomes the amount of information acquired during a unit period. The information presentation timing adjustment module adjusts the timing according to the user's behavior notified from the behavior monitoring module. The information output module presents the adjusted information to the user at the adjusted timing. See Japanese Unexamined Patent Application Publication No. 2000-99441.

Another proposed technology aims at collecting information from information sources or receiving information supplied to users and presenting the information to users. The importance determination portion and the presentation deadline determination portion respectively determine the importance of the information and the presentation deadline of the information from the beginning of the information stored in the information storage portion. The busy level estimation portion estimates the busy level at each time based on the busy level entered by the user and the clock. Based on the determination result and the busy level, the information presentation determination portion determines whether it is time to present the information to the information presentation portion. The information presentation portion presents the information to be presented. See Japanese Unexamined Patent Application Publication No. Hei8 (1996)-241256.

One case of the above-described information provision recognizes unfavorable motions or postures (hereinafter collectively referred to as "motions") of those who are working or in training, and provides information to promote the improvement of the motions.

When the existing art is applied to such a case, information is presented after a series of tasks or training. However, it is difficult for a person who was working or in training to intuitively recognize at what point of the motion the information suggests the improvement. Therefore, even if the information is presented, a subject cannot fully understand the information, failing to sufficiently provide the effect of improving the motion.

It is an object of the present invention to provide a technology capable of efficiently transmitting information appropriate for improving motions to a person in motion.

SUMMARY

A motion evaluation system according to the present invention solves the above-described issues and includes an information processing device that includes a communication device, a storage device, and an arithmetic device. The communication device communicates with a sensor to observe a motion of a user. The storage device stores reference information defining various states of the motion and various information suggesting improvement of the motion. The arithmetic device performs a process to acquire motion data acquired by observing the user through the use of the sensor via the communication device, check the motion data against information about the correctness of motions in the reference information to determine the state of motion of the user, and specify, as an improvement, a motion in a state to be improved among the motions. The arithmetic device performs a process to check the motion data after the motion corresponding to the improvement against information about busy levels of the user among the reference information to specify a busy level of the user. The arithmetic device performs a process to extract, as improvement suggestion information about the improvement, information with different contents at each of multiple times from the storage device based on the improvement and a rule predetermined according to each situation of the busy level and output the information to an information presentation device for the user.

A motion evaluation device according to the present invention includes a communication device, a storage device, and an arithmetic device. The communication device communicates with a sensor to observe a motion of a user. The storage device stores reference information defining various states of the motion and various information suggesting improvement of the motion. The arithmetic device performs a process to acquire motion data acquired by observing the user through the use of the sensor via the communication device, check the motion data against information about the correctness of motions in the reference information to determine the state of motion of the user, and specify, as an improvement, a motion in a state to be improved among the motions. The arithmetic device performs a process to check the motion data after the motion corresponding to the improvement against information about busy levels of the user among the reference information to specify a busy level of the user. The arithmetic device performs a process to extract, as improvement suggestion information about the improvement, information with different contents at each of multiple times from the storage device based on the improvement and a rule predetermined according to each situation of the busy level and output the information to an information presentation device for the user.

A motion evaluation method according to the present invention is implemented by an information processing device including a communication device that communicates with a sensor to observe a motion of a user and a storage device that stores reference information defining various states of the motion and various information suggesting improvement of the motion. The motion evaluation method performs a process to acquire motion data acquired by observing the user through the use of the sensor via the communication device, check the motion data against information about the correctness of motions in the reference information to determine the state of motion of the user, and specify, as an improvement, a motion in a state to be improved among the motions. The motion evaluation method performs a process to check the motion data after the motion corresponding to the improvement against information about busy levels of the user among the reference information to specify a busy level of the user. The motion evaluation method performs a process to extract, as improvement suggestion information about the improvement, information with different contents at each of a plurality of times from the storage device based on the improvement and a rule predetermined according to each situation of the busy level and output the information to an information presentation device for the user.

The present invention can efficiently transmit information appropriate for improving motions to a person in motion.

BRIEF DESCRIPTION OF DRAWINGS

FIGS. 8A to 8F are diagrams illustrating graphs of a workload and a feature amount according to the present embodiment;

FIG. 9 is a diagram illustrating the concept of busy level evaluation according to the present embodiment;

FIG. 17 is a diagram illustrating the configuration of a personal attribute table according to the present embodiment.

DESCRIPTION OF EMBODIMENTS

Figure 1:
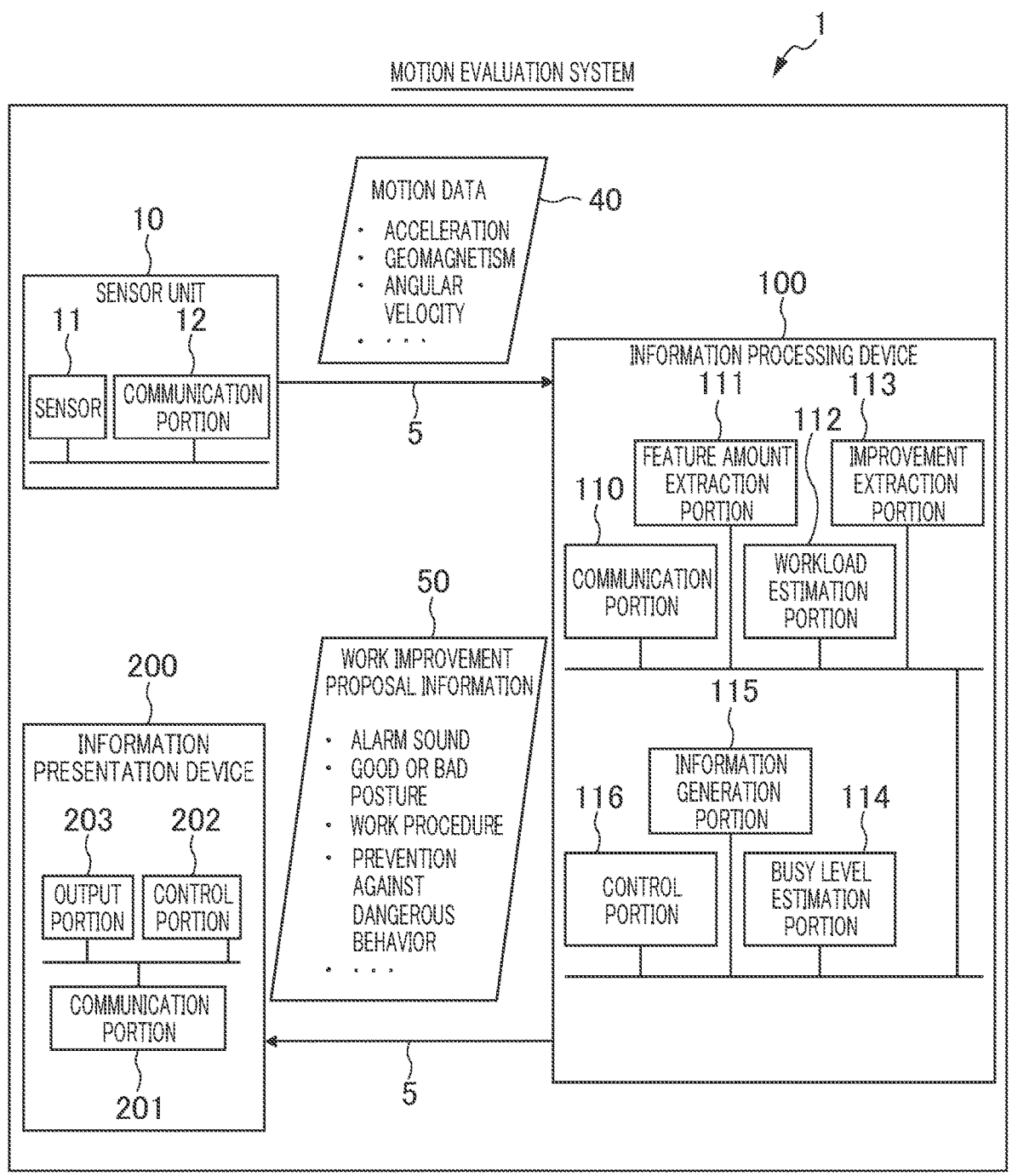
FIG. 1 is a diagram illustrating an entire block of the motion evaluation system according to the present embodiment.

The present embodiment will be described in detail through the use of the drawings. However, the present invention should not be construed to be limited to the contents of the embodiments described below. It is easily understood by those skilled in the art that various modifications may be made in the specific configurations without departing from the spirit and scope of the present invention.

In the configurations of the invention described below, the same portions or portions having similar functions may use the same reference numerals in different drawings, and redundant description may be omitted.

When there are multiple elements having the same or similar functions, the same reference numeral may be given different additional characters. However, additional characters may be omitted when there is no need to make a distinction among the elements.

The notations such as "first," "second," and "third" in this specification, for example, are used to identify composing elements and do not necessarily limit the number of items, order, or contents thereof.

A number to identify a composing element is used for each context. A number used in one context does not necessarily indicate the identical configuration in other contexts.

A composing element identified by a given number may also function as a composing element identified by another number.

Positions, sizes, shapes, and ranges of respective configurations shown in the drawings, for example, may not represent actual ones to facilitate understanding of the invention. Therefore, the present invention is not necessarily limited to the positions, sizes, shapes, and ranges disclosed in the drawings, for example.

Throughout the present specification, each composing element represented in the singular form shall imply the plural form unless explicitly stated in the context.

Preconditions on the Description Below

A person subject to motion evaluation, namely, a person in motion is hereinafter referred to as a user. Suppose the user needs to be notified of which part of the user motion to be improved. Then, it is first necessary to estimate the quality of the user motion (motion estimation) and specify an issue in the motion (extraction of improvements).

It is also necessary to estimate the busy level of the user from the motion situation of the user (estimation of busy level) and determine the timing to present the information (determination of the information presentation time) and its contents (determination of the presentation information content) according to the busy level.

Finally, the information is presented to the user according to the information presentation time and content determined as described above (presentation of improvement points). The timing to present the information occurs several times. The presentation content may be adjusted according to each timing.

Here, "motion" signifies general work in industry or agriculture, for example, as well as general physical motion performed by a human for predetermined purposes such as dance, gymnastics, and playing musical instruments, for example.

The purpose is to specifically specify which part of the motion is disadvantageous. For this purpose, it is favorable to evaluate the motion of a specific part of the user's body at a specific timing.

Such technology can be used as a work support system or an education system, for example. The work support system can be used for training in maintenance of facilities and devices, for example. The education system can be used to practice dance or yoga poses, for example.

FIRST EMBODIMENT

Overall System Configuration

FIG. 1 is a diagram illustrating an overall block of a motion evaluation system 1 according to the present embodiment. The motion evaluation system 1 includes a sensor unit 10, an information processing device 100, and an information presentation device 200. The sensor unit 10, the information processing device 100, and the information presenting device 200 are communicably connected via a wired or wireless network 5.

Figure 2:
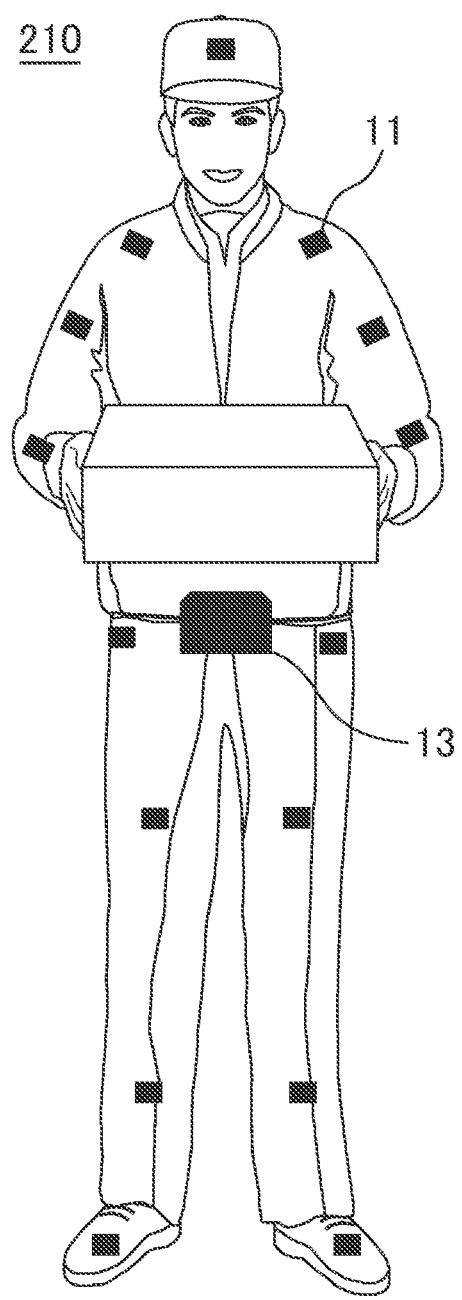
FIG. 2 is a diagram illustrating a mode of attaching sensors according to the present embodiment.

The sensor unit 10 includes a sensor 11 and a communication portion 12. The sensor 11 is wearable so that it can be attached to the user's body, for example. The sensor 11 can be assumed to be available as a motion sensor that observes the user's motion (such as acceleration) but is not limited thereto. FIG. 2 illustrates an example where a user 210 wears the sensor 11.

The sensor 11 notifies a sensor hub 13, for example, of motion data such as acceleration acquired from the observation directly or via another sensor. The connection between the sensor 11 and the sensor hub 13 may be wired or wireless. The sensor hub 13 is one of the sensor units 10 or at least includes a communication portion.

The sensor hub 13 wirelessly, for example, transmits the motion data 40 transmitted from the sensors 11 to the information processing device 100 via the communication portion. The sensor 11 and the sensor hub 13 are assumed to be supplied with power from a battery (unshown), for example. The arrangement of the sensors 11 in FIG. 2 is an example. The sensors may be attached to parts of the whole body as illustrated in FIG. 2. The sensors may be attached to only part of the body such as the upper body only or the lower body only depending on the motion to be evaluated.

The type or mounting location of the sensor 11 may be selected from one or more known types of sensors according to the motion to be evaluated.

To directly evaluate the body motions of the user 210, it is favorable to use sensors capable of measuring positions and motions of each part of the body of the user 210. For example, an acceleration sensor or a position sensor is applicable. Besides, it may be favorable to adopt sensors used for gyro, geomagnetism, video, audio, electromyography, and angular velocity, for example.

The user 210 attached with a reflection marker may be captured on a video camera, for example, to measure positions and motions of each part of the body. The following description assumes and explains situations where an acceleration sensor is used as an example of the sensor 11.

Example of Hardware Configuration

Figure 3:
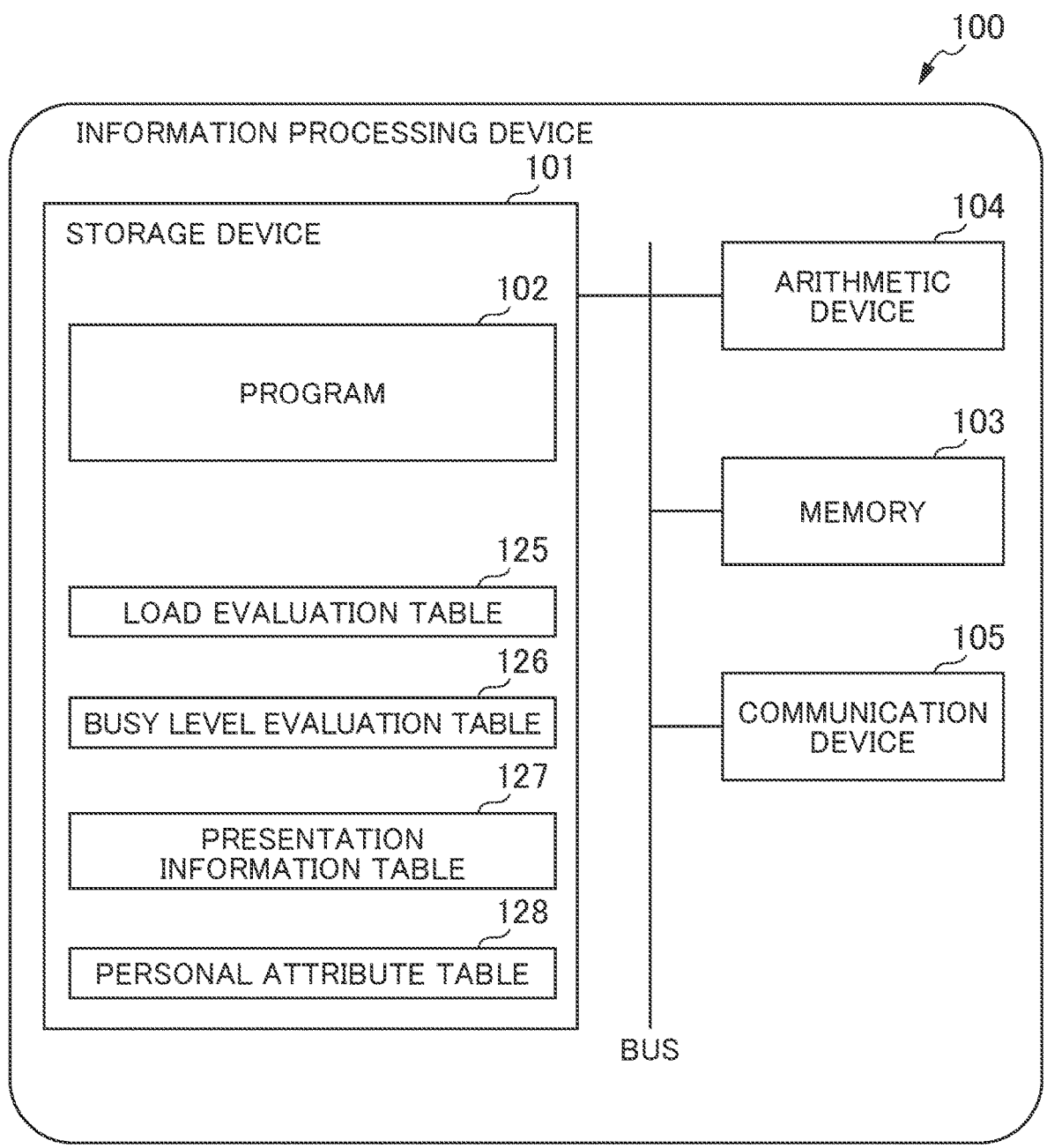
FIG. 3 is a diagram illustrating a hardware configuration of a calculator according to the present embodiment.

The description below explains the hardware configuration of the above-mentioned information processing device 100 based on FIG. 3. The information processing device 100 includes a storage device 101, memory 103, an arithmetic device 104, and a communication device 105.

The storage device 101 is composed of an appropriate non-volatile storage element such as an SSD (Solid State Drive) or a hard disk drive.

The memory 103 is composed of a volatile memory element such as RAM.

The arithmetic device 104 is a CPU that reads the program 102 stored in the storage device 101 into the memory 103 and executes the program 102 to perform overall control over the device itself as well as various determinations, calculations, and control processes.

The communication device 105 is a network interface card that connects to the appropriate network 5 and handles communication processing with other devices.

The storage device 101 stores at least a load evaluation table 125, a busy level evaluation table 126, a presentation information table 127, and a personal attribute table 128 in addition to the program 102 that implements functions required for the information processing device 100 according to the present embodiment.

In addition to the illustrated configuration, the information processing device 100 may include an input device such as a keyboard, a mouse, or a microphone that accepts key or voice input from the user. Similarly, the information processing device 100 may include an output device such as a display or a speaker that outputs processing data in the arithmetic device 104.

As will be described, various motions corresponding to the motion evaluation method according to the present embodiment shall be actualized by a program the information processing device 100 as a motion evaluation device reads into memory, for example, and executes. The same applies to the description below.

According to the present embodiment, functions such as calculation and control correspond to the functional blocks illustrated in FIG. 1 and achieve the predetermined processes in collaboration with other hardware under the condition that the arithmetic device 104 executes the program 102 stored in the storage device 101.

The above-described configuration using the standalone information processing device may use other networked computers to replace any part of the input device, the output device, the processing device, and the storage device. Hardware such as FPGA (Field Programmable Gate Array) or ASIC (Application Specific Integrated Circuit) can also provide functions comparable to those provided by the software in the present embodiment. For example, FPGA may provide a neural network to be described.

Functional Blocks

The information processing device 100 includes functional blocks such as a communication portion 110, a feature amount extraction portion 111, a workload estimation portion 112, a workload estimation portion 112, a busy level estimation portion 114, an information generation portion 115, and a control portion 116. These are described below.

The communication portion 110 receives motion data 40 transmitted from the communication portion 12 of the sensor unit 10. The communication portion 110 transmits work improvement proposal information 50 as information about the improvement suggestion to the information presentation device 200.

The feature amount extraction portion 111 extracts the intended feature amount from the motion data 40. The workload estimation portion 112 is supplied with, as input, the motion data 40 or the feature amount extracted by the feature amount extraction portion 111 and estimates the workload according to the user's working posture. The present embodiment estimates the posture based on the motion data 40. The feature amount extraction portion 111 or the workload estimation portion 112 can be configured through the use of a neural network, for example.

The workload estimation portion 112 extracts improvements using the feature amount from feature amount extraction portion 111 and the workload from the workload estimation portion 112.

The busy level estimation portion 114 is supplied with, as input, the motion data 40 or the feature amount extracted by feature amount extraction portion 111 to estimate the busy level of a user work.

The information generation portion 115 generates the work improvement proposal information 50 for notification to the user 210 based on the improvements extracted by the workload estimation portion 112 and the busy level extracted by the busy level estimation portion 114.

One piece of the work improvement proposal information 50 is not always generated at a time. Multiple pieces of information with different contents may be generated. The work improvement proposal information 50 is transmitted from the communication portion 110 to the information presentation device 200. The control portion 126 controls the entire operation sequence of the information processing device 100.

The information presentation device 200 is also a type of information processing device. For example, the information presentation device 200 is available as a mobile information terminal the user 210 can carry but is not limited thereto. A typical hardware configuration includes an input device, an output device, a processing device, and a storage device. If the purpose is only to notify the user 210 of the information, it is sufficient to provide the communication portion 201 to receive the information from the information processing device 100, an overall control portion 202, and an output portion 203 to display the information. There may be available a device capable of printing information on paper media. The output portion 203 represents a liquid crystal display, a speaker, or a vibrator, for example.

Feature Amount Extraction Portion

Figure 4:
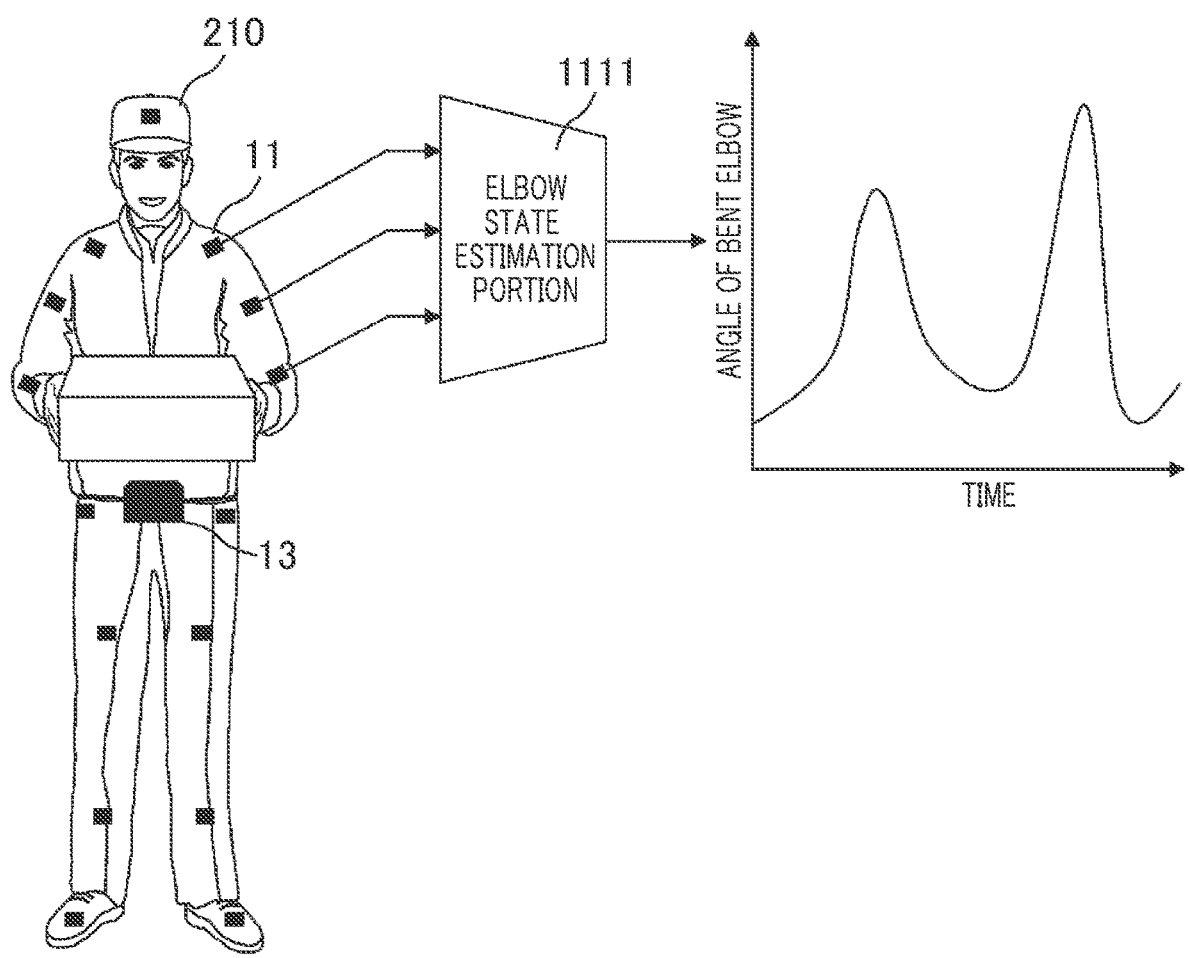
FIG. 4 is a diagram illustrating the operation concept of an elbow state estimation portion according to the present embodiment.

FIG. 4 is a conceptual diagram illustrating the function of the feature amount extraction portion 111. The feature amount extraction portion 111 extracts the feature amount to evaluate loads on working postures of the user 210. In this case, for example, a system designer defines one or more feature amounts depending on the purpose of motion evaluation.

For example, one or more of an elbow bending angle, a waist height, a head orientation, and a leg opening angle can be defined as the feature amount. These feature amounts are associated with the states of moving parts of the user's body such as the features of motions of each joint.

As a premise, a predetermined person in charge, for example, attaches the sensor 11 to the user 210 to extract the required feature amount. The sensor 11 acquires motion data having the required physical quantity. The feature amount extraction portion 111 acquires the motion data 40 from any one or more of the sensors 11 mounted on the user 210 and uses the motion data 40. The description below explains an example of estimating the elbow bending angle through the use of an acceleration sensor.

FIG. 4 illustrates an elbow state estimation portion 1111 included in the feature amount extraction portion 111. The elbow state estimation portion 1111 extracts elbow bending angles of the user 210 from the motion data observed by the sensor 11. As illustrated in FIG. 4, the elbow state estimation portion 1111 acquires motion data from the three sensors 11 attached to the left arm of the user 210 and determines a left elbow bending angle based on the motion data. The motion data is observed every unit time and is provided for the elbow state estimation portion 1111. Therefore, a result of determining the left elbow bending angle is also acquired as chronological data.

To extract feature amounts other than elbow bending angles, the feature amount extraction portion 111 can include an additional portion to determine motions of the target part such as a waist height extraction portion or a head orientation extraction portion, for example, similar to the elbow state estimation portion 1111.

The elbow state estimation portion 1111 can be configured as a deep neural network (DNN), for example, and can be trained under known supervised learning. An event to be learned is used as a model to show the correspondence between the motion data (such as acceleration data) acquired from the sensor 11 and a correct elbow bending angle (teacher data determined by the person in charge, for example) acquired from the motion data as input.

The elbow state estimation portion 1111 can also estimate the elbow bending angle according to ordinary calculation using acceleration data from the sensor 11 instead of the above-mentioned DNN.

When the elbow bending angle is estimated from the acceleration, the elbow state estimation portion 1111 acquires an observed value in the initial state of the user 210 from the sensor 11 and uses the value. For this purpose, the user 210 previously may need to maintain a predetermined posture (such as an upright posture). The position of the sensor 11 may be separately detected. Alternatively, the sensor 11 may use a position sensor instead of the acceleration sensor. The type of sensors can be freely selected according to the feature amount to be estimated.

During system operation, the storage device stores the extracted feature amount as chronological data corresponding to the types.

Workload Estimation Portion

The workload estimation portion 112 uses the motion data 40 from the sensor 11 and the feature amount extracted by the feature amount extraction portion 111 as inputs to estimate a workload corresponding to the working posture.

Figure 5:
FIG. 5 is a diagram illustrating the configuration of a load evaluation table according to the present embodiment.
Figure 6:
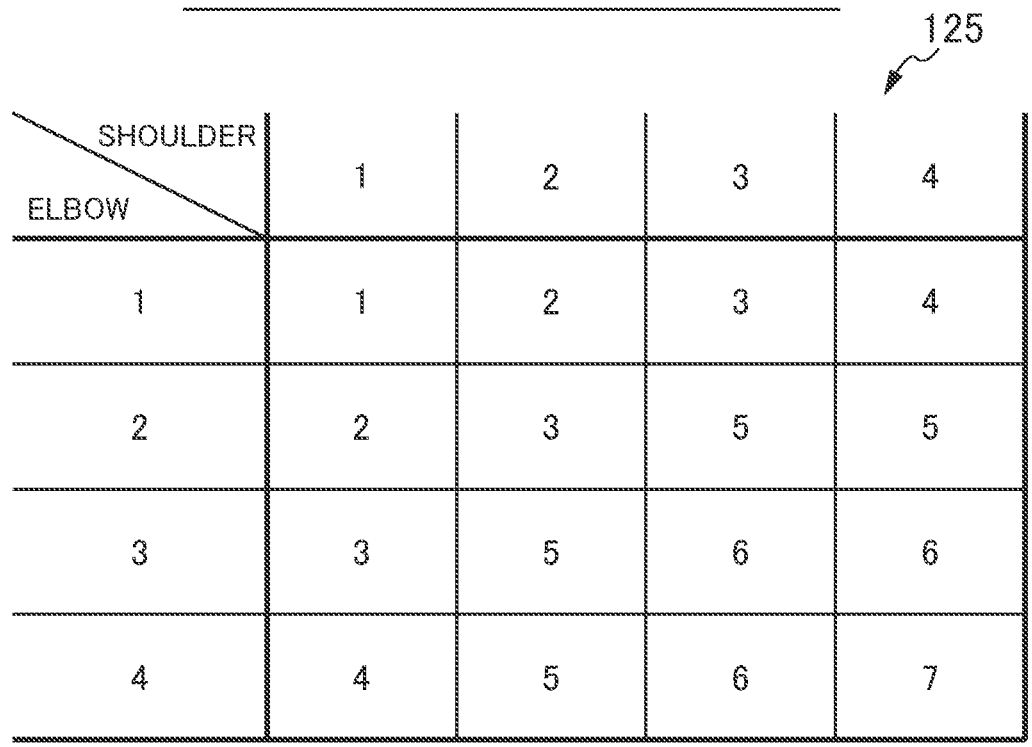
FIG. 6 is a diagram illustrating the configuration of a load evaluation table according to the present embodiment.

FIGS. 5 and 6 illustrate the load evaluation table 125 used for the workload estimation in the workload estimation portion 112.

The load evaluation table 125 in FIG. 5 is used to calculate a load applied to the elbow based on the elbow bending angle extracted in the feature amount extraction portion 111. As illustrated in FIG. 5, an increase in the elbow bending angle increases a load on the elbow and increases the corresponding load score.

The configuration illustrated here is just an example. The load score corresponding to the elbow bending angle may differ from the form illustrated in FIG. 5. For example, it may be favorable to use the load score defined in the evaluation method called RULA (Rapid Upper Limb Assessment).

Load scores may be defined for multiple body parts and may be combined to define a load score for a larger body part. For example, as illustrated in FIG. 6, the load evaluation table 125 estimates a score of load applied to the arm by determining a combination of load scores for the elbow and the shoulder.

Similar to FIG. 5, the configuration of FIG. 6 is just an example. The combination of body parts and the scores defined by the combination may differ from the form illustrated in FIG. 6. For example, it may be favorable to use the combinations and scores as defined in RULA.

Methods of estimating workload are not limited to the method using the correspondence table described above. There may be a method proving the similar effect such as automatically estimating workloads using machine learning, for example.

Improvement Extraction Portion

Figure 7A:
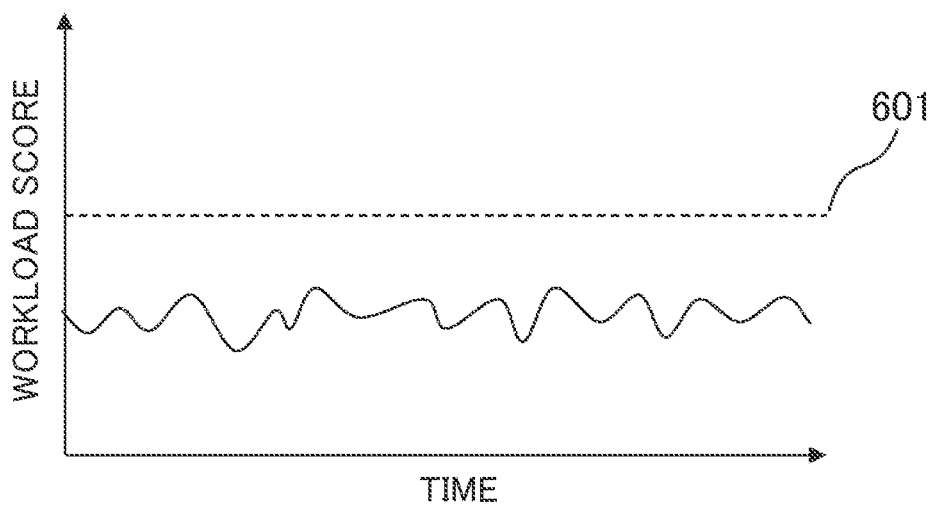
FIG. 7A is a diagram illustrating a graph of workload score for a correct working posture according to the present embodiment.
Figure 7B:
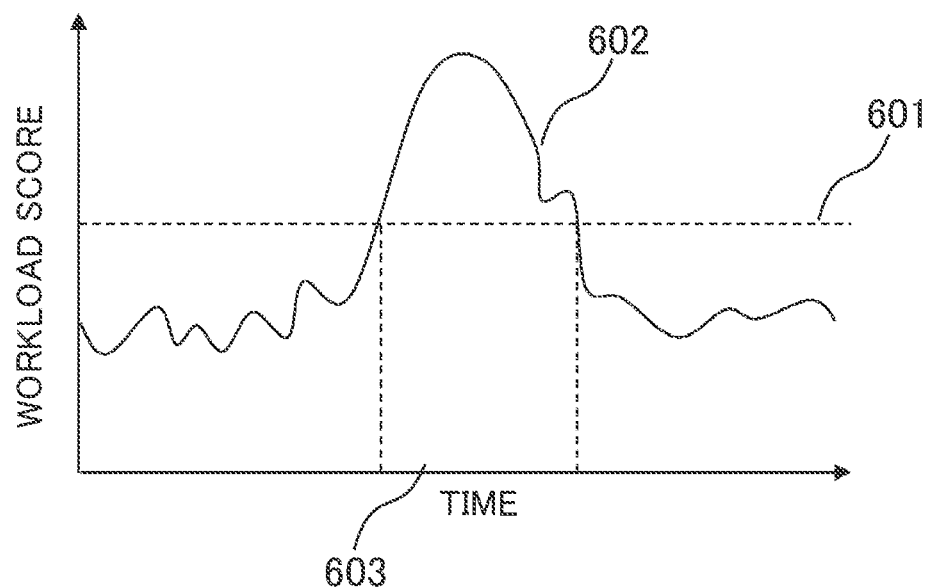
FIG. 7B is a diagram illustrating a graph of workload score for an incorrect working posture according to the present embodiment.

FIG. 7A illustrates a graph of workload scores when working in the correct posture. FIG. 7B illustrates a graph of workload scores when working in working postures including incorrect postures. Since the workload score is chronological data, the horizontal axis shows the time and the vertical axis shows workload scores.

In these examples, the workload score for the working posture including incorrect postures contains a region 602 where the workload increases during a given time slot. The workload estimation portion 112 determines an incorrect working posture when the workload score exceeds a predetermined threshold value 601 for a specified period or longer. Other techniques capable of achieving the same effect can be used to detect incorrect working postures.

For example, incorrect working postures may be determined based on relative variations of the workload score without the use of the threshold value. The threshold value 601 may be variable rather than fixed.

When recognizing an incorrect working posture, the workload estimation portion 112 notifies the workload estimation portion 112 of the information about the time slot 603 corresponding to the incorrect working posture.

The workload estimation portion 112 acquires feature amount data including the corresponding time slot from the feature amount extraction portion 111. The workload estimation portion 112 compares the feature amount data acquired from the above-mentioned feature amount extraction portion 111 with the transition of the feature amount data previously stored in the storage device for works in the correct posture to specify the feature amount causing the difference between both to be greater than or equal to that specified. During the system operation, the storage device stores the estimated workload score as chronological data.

The description below explains example operations of the workload estimation portion 112 based on FIG. 8. FIG. 8A shows the workload score in the correct posture as a reference. FIG. 8C shows the score of an elbow bending angle as one of the feature amounts in the correct posture. FIG. 8E shows the score of a shoulder joint angle as one of the feature amounts in the correct posture.

FIG. 8B shows the workload score of the user. FIG. 8D shows the score an elbow bending angle one of the user's feature amounts including incorrect working postures. FIG. 8F shows the score of a shoulder joint angle as one of the user's feature amounts.

In terms of "elbow bending angle" as the feature amount, it is possible to confirm that there is a difference between the correct posture and the user (incorrect posture) in the size of the feature amount at time slot 801. This can be determined based on a large difference in the workload scores.

In terms of "shoulder joint angle" as the feature amount, however, there is no difference between both. Therefore, it is possible to determine that the motion evaluation system 1 needs to provide the user with an improvement concerning the "elbow bending angle" at the time slot 801 corresponding to the incorrect working posture.

As above, the workload estimation portion 112 extracts part of the entire motion of the user's body as the motion to be improved. After performing the above-described analysis, the workload estimation portion 112 transmits the feature amount to be improved and the difference from the correct posture, for example, to the information generation portion 115.

Busy Level Estimation Portion

The busy level estimation portion 114 estimates the user's busy level by using the motion data 40 from the sensor and the feature amount extracted by the feature amount extraction portion 111 as inputs.

FIG. 9 is a conceptual diagram illustrating the function of the busy level estimation portion 114. The busy level estimation portion 114 recognizes the user's behavior and estimates a busy level based on the behavior.

For example, a system designer defines one or more busy levels depending on the purpose of the education system. For example, it is possible to recognize the user's behavior through the use of the motion data 40 or the feature amount extracted by the feature amount extraction portion 111 and define a busy level according to the behavior. The description below explains an example case of recognizing a work through the use of an acceleration sensor.

FIG. 9 illustrates a work recognition portion 1141 included in the busy level estimation portion 114 to recognize works of the user based on the motion data acquired from the sensor 11.

As illustrated in FIG. 9, the work recognition portion 1141 acquires the motion data 40 concerning the user 210 from the sensor 11 mounted on the whole body of the user 210 and determines a current work based on the motion data 40. The information about works is acquired as chronological data. Concurrently with the work determination, the busy level evaluation table 126 can be used to specify the busy level of the work.

According to the example in FIG. 9, the work recognition portion 1141 applies the motion data 40 acquired from the sensor 11 to the busy level evaluation table 126 and determines the corresponding work as "carrying load." The work of "carrying load" is given busy level "2" which is then assumed to be the busy level.

According to the busy level evaluation table 126 illustrated in FIG. 9, a "pattern" defines the correspondence between each work and the motion data 40. The busy level estimation portion 114 checks the pattern of each work against the motion data 40 and determines that the user is performing the "work" whose "pattern" matches a chronological change in the motion indicated by the motion data 40.

The work recognition portion 1141 can be configured as a deep neural network (DNN), for example, and can be trained under known supervised learning. Input to the work recognition portion 1141 is not limited to the motion data 40 from the sensor 11. The feature amount extracted by the feature amount extraction portion 111 may be also used as input at the same time. Alternatively, only the feature amount may be used as input.

The work recognition portion 1141 is not necessarily limited to the DNN. It may be favorable to use other techniques proving the similar effect.

During the system operation, the storage device stores the estimated work and busy level as chronological data according to the types.

The method of estimating busy levels is not limited to the above-described behavior recognition. There may be a method proving the similar effect such as estimating busy levels based on the user's notification.

Information Generation Portion

The information generation portion 115 determines when to notify what contents of information how often, based on the information about the improvement received from the workload estimation portion 112 and the information about the busy level received from the busy level estimation portion 114. The information generation portion 115 uses graphic data or audio data, for example, previously stored in the presentation information table 127 to generate the work improvement proposal information 50 to be presented to the user.

Figure 10:
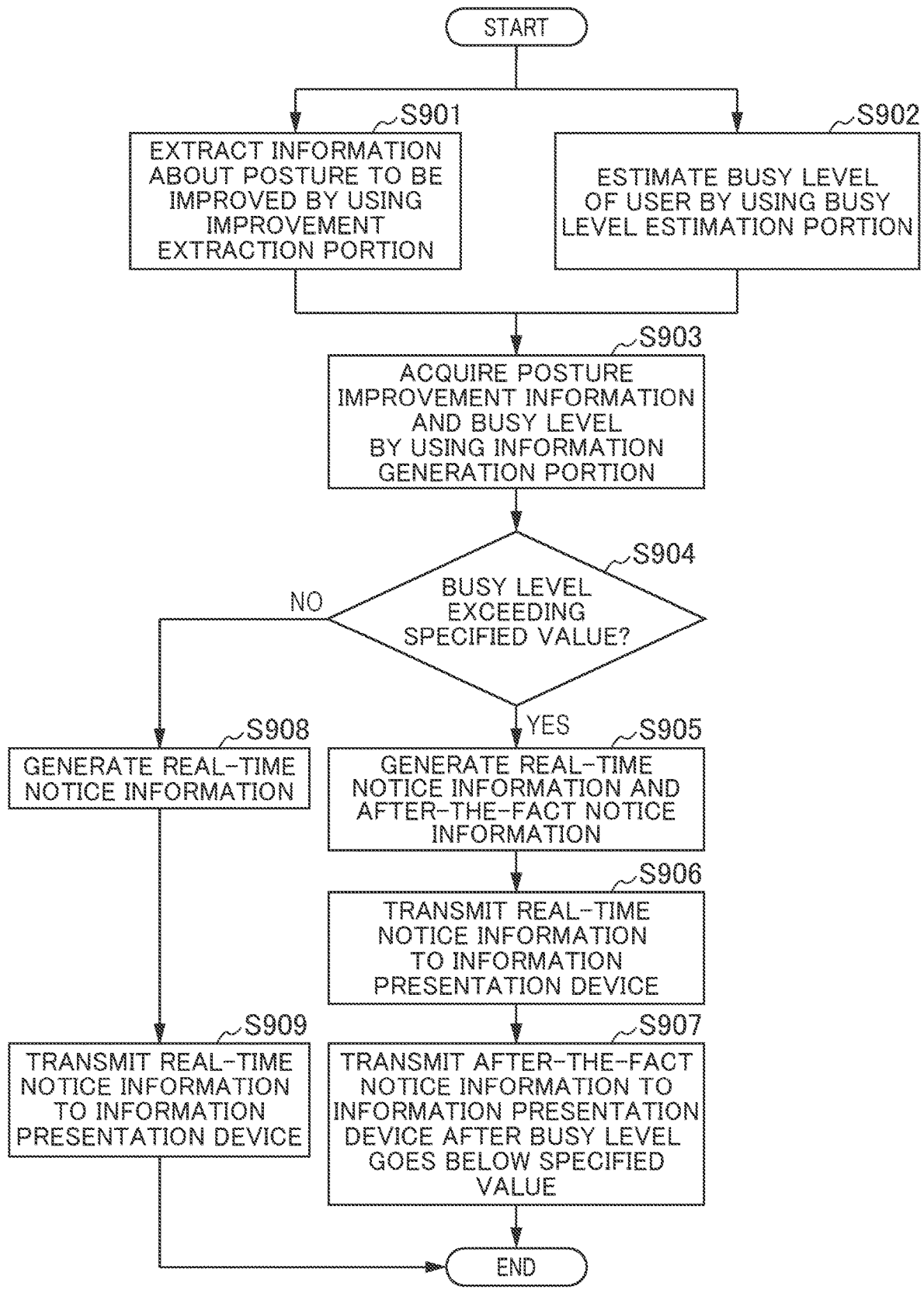
FIG. 10 is a diagram illustrating a flow of the motion evaluation method according to the present embodiment.

FIG. 10 is a flow chart illustrating one method for generating the work improvement proposal information 50. At process S901, the workload estimation portion 112 extracts working posture information needed for the user to improve from the motion data 40 received by the communication portion 110 from the sensor 11 and the feature amount extracted by the feature amount extraction portion 123.

At process S902, the busy level estimation portion 114 estimates a busy level for the user from the motion data 40 and the feature amount described above. The working posture information and the busy level are chronological data.

At process S903, the information generation portion 115 receives the working posture information and busy level at the current time from the workload estimation portion 112 and the busy level estimation portion 114 described above.

At process S904, the information generation portion 115 determines whether the busy level acquired at S903 exceeds a specified value.

Figure 11:
FIG. 11 is a diagram illustrating the configuration of a presentation information table according to the present embodiment.

As a result of the above-described determination, the busy level may exceed the specified value (S904: YES). In this case, at process S905, the information generation portion 115 specifies the content corresponding to the feature amount indicated by the working posture information as real-time notice information that contains "elbow" as the target part in the presentation information table 127 (see FIG. 11), for example. Similarly, after-the-fact notice information is also specified. The real-time notice information and the after-the-fact notice information are thus generated.

At process S906, the information generation portion 115 transmits the above-described real-time notice information to the information presentation device 200. At process S907, the information generation portion 115 retains the after-the-fact notice information until the above-described busy level falls below the specified value. If the busy level falls below the specified value (S904: NO), the information generation portion 115 transmits the after-the-fact notice information to the information presentation device 200.

The real-time notice information is notified when the user's busy level is high. The after-the-fact notice information is notified after the user's busy level decreases. Therefore, these two types of information may have different contents.

Specifically, the real-time notice information is intended only to notify that something needs to be improved presently without interfering with the user's work. Specifically, it may be favorable to provide extremely simple information such as warning sound or vibration for several seconds.

The after-the-fact notice information is provided after the user's busy level decreases. Therefore, the information may be more detailed and complicated than the graphic data or audible instructions to attract the user's attention and more fully impress the contents of the improvements.

If the busy level does not exceed the specified value (S904: NO), the information generation portion 115 generates the real-time notice information at process S908. The real-time notice information generated at process S905 may differ from the real-time notice information generated at process S908 in the contents. The information may be provided as an integration of the real-time notice information generated at process S905 and the after-the-fact notice information or as a summary of these. The work improvement proposal information 50 is transmitted from the communication portion 110 to the information presentation device 200.

The present embodiment acquires the user's motion data 40, previously provides data related to the working postures, and thereby extracts the user's working posture to be improved. Technology such as deep learning is used to recognize the work being performed by the user and estimate the busy level.

The use of these in combination makes it possible to notify working posture improvements through the use of a simple method such as warning sound or vibration during the work at a high busy level and propose more detailed and correct motions when the busy level decreases. It is possible to more comprehensively provide the user with both types of information, namely, a missed opportunity for improvement and a specific approach to the improvement.

Information Presentation Device

Figure 12:
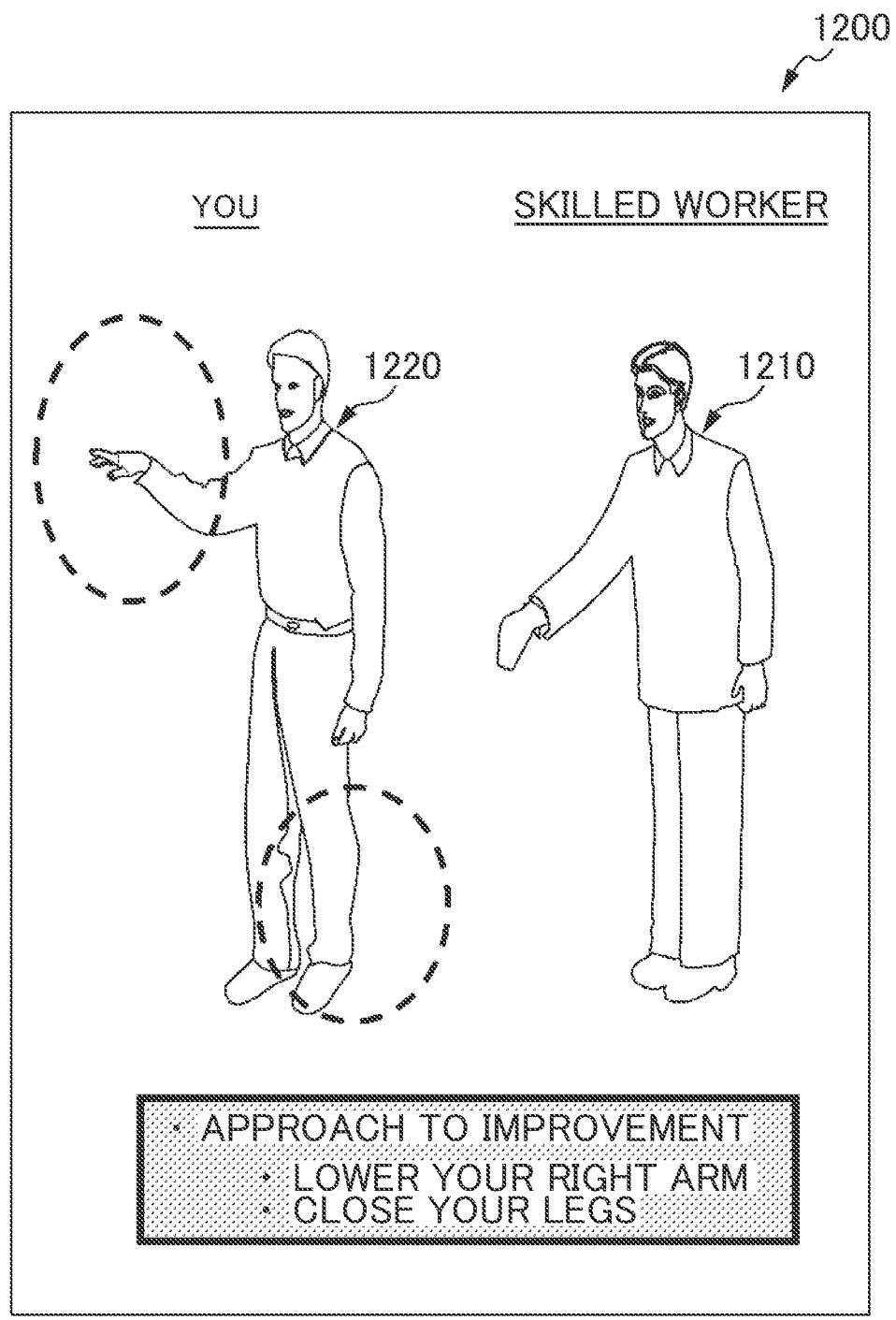
FIG. 12 is a diagram illustrating an output according to the present embodiment.

FIG. 12 illustrates an example screen on the output portion 203 of the information presentation device 200. A screen 1200 displays the feature amount to be improved by using a humanoid model to aid in the understanding of the user.

On the screen 1200, the information presentation device 200 may provide a comparison by displaying the correct working posture 1210 and the user's model 1220 to be placed side by side or overlapped.

In the example of FIG. 12, the information presentation device 200 uses computer graphics (CG) to provide an improvement on the position of the right arm and the opening angle of the legs based on the information from the workload estimation portion 112.

It may be favorable to output text or voice or generate oscillation to aid in the understanding of the user. Methods for generating text, speech, or vibration patterns are available from captioning and speech synthesis technologies using machine learning or displays using prepared patterns. The use of moving CG is particularly effective for the after-the-fact notice information.

Effects of the First Embodiment

As above, the first embodiment estimates the working posture of a person in motion, extracts the motion resulting from a suspected site corresponding to the working posture, and concurrently estimates the busy level of the user. It is possible to propose improvements multiple times according to the busy level of the user.

It is possible to more comprehensively provide the user with both types of information, namely, at what point the user took a posture to be improved and a specific approach to the improvement.

During a squat exercise, for example, an incorrect movement of the lower back or knees hinders an appropriate effect of the exercise or may injure the lower back or knees depending on circumstances.

In such a case, the information presentation according to publicly known techniques cannot fully attract the user's attention during the exercise. The information is provided after a series of exercises.

However, the squat motion is practically repeated many times during the exercise. Even if the information is presented after the exercise, it is difficult to understand which motion was incorrect at what timing.

Contrastingly, the present approach provides simple information such as a warning sound once at the timing of the incorrect motion and provides anew detailed information after a series of exercises. This makes it possible to be more aware of the incorrect motion and improve the learning effect.

SECOND EMBODIMENT

The first embodiment provides the user with only the information to improve the posture. As another example, when no improvement is found, the workload estimation portion 112 can transmit information about the motion being correctly made to the information generation portion 115. The workload estimation portion 112 can also provide the user with information to positively evaluate the user's motion as being correct by allowing the information generation portion 115 to extract such information from the presentation information table 127.

Information to positively evaluate the user may be also presented in a simple way when the user is busy at work, for example. Detailed information may be presented when the busy level decreases. This makes it possible to encourage the user to work in the correct posture.

THIRD EMBODIMENT

The first and second embodiments cause no change in the information generated by the information generation portion 115 even if the workload estimation portion 112 repeatedly extracts similar improvements.

As another example, when the same improvement is found repeatedly in the workload estimation portion 112, the information generation portion 115 can count the number of repetitions and further emphasize the content of the notification If the number of repetitions exceeds a predetermined count.

Figure 13:
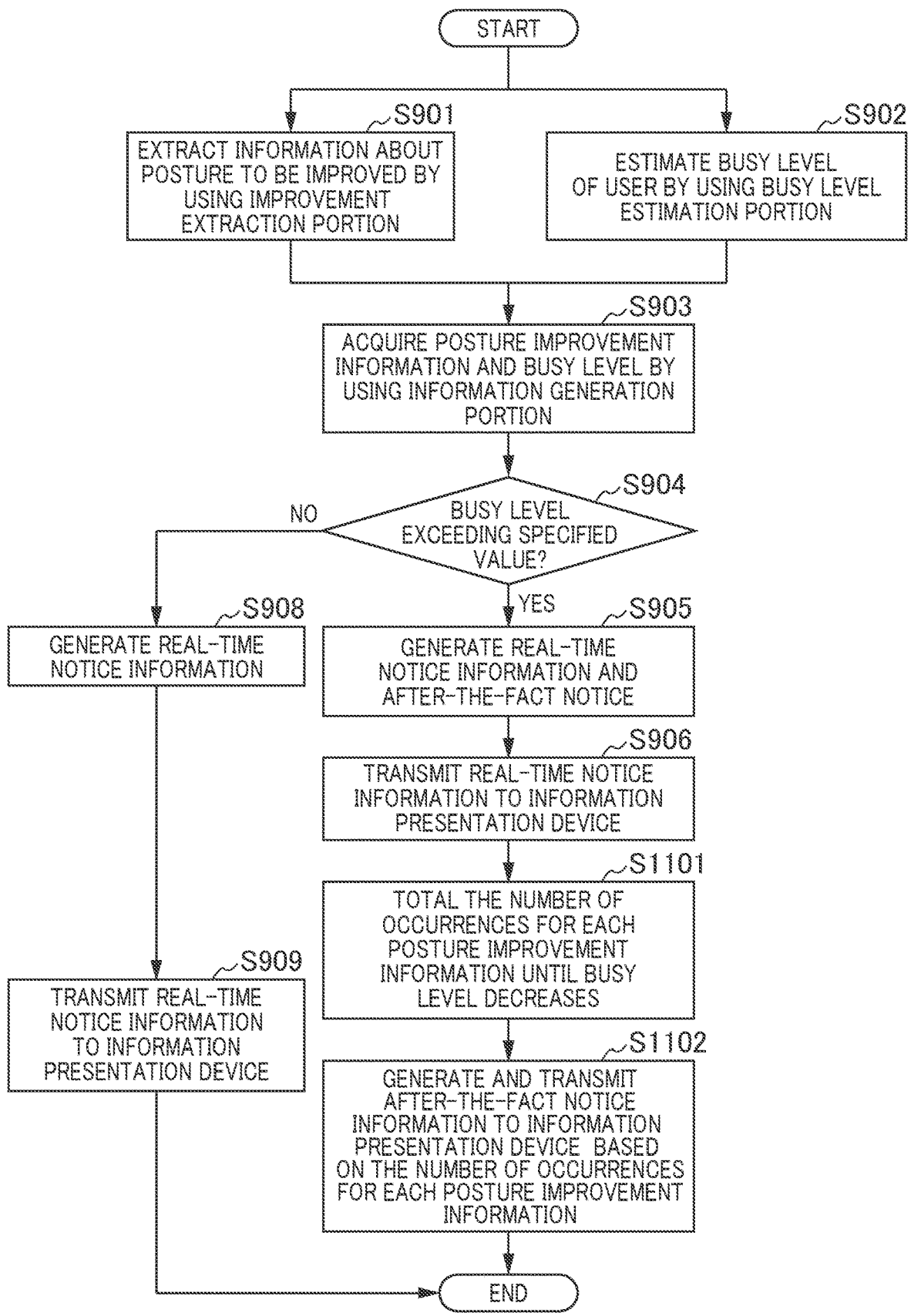
FIG. 13 is a diagram illustrating a flow of the motion evaluation method according to the present embodiment.

FIG. 13 is a flowchart illustrating one technique to change the contents of the work improvement proposal information 50 to be generated according to the number of repeatedly occurred similar improvements.

The processes up to S906 in the flowchart are equal to those in the flowchart in FIG. 10. The description below explains S1101 and later.

At S1101, the information generation portion 115 totals the number of occurrences for each type of posture improvement information until the user's busy level decreases.

At S1102, the information generation portion 115 changes the contents of the after-the-fact notice information extracted from the presentation information table 127 according to the number of occurrences of each posture improvement information and transmits the after-the-fact notice information to the information display device 150.

The contents of the after-the-fact notice information may be changed by using colors emphasizing the notation in CG for frequently occurring information, boldfacing letters in text, or changing colors, for example. This enables users to focus on learning working postures that are more likely to go wrong.

FOURTH EMBODIMENT

The first, second, and third embodiments determine whether to generate only the real-time notice information or generate the after-the-fact notice information as well and notify the information multiple times, only based on the worker's busy levels.

As another example, when the workload estimation portion 112 extracts a highly urgent improvement, it is also possible to immediately present the information even if the busy level exceeds a specified value.

Figure 14:
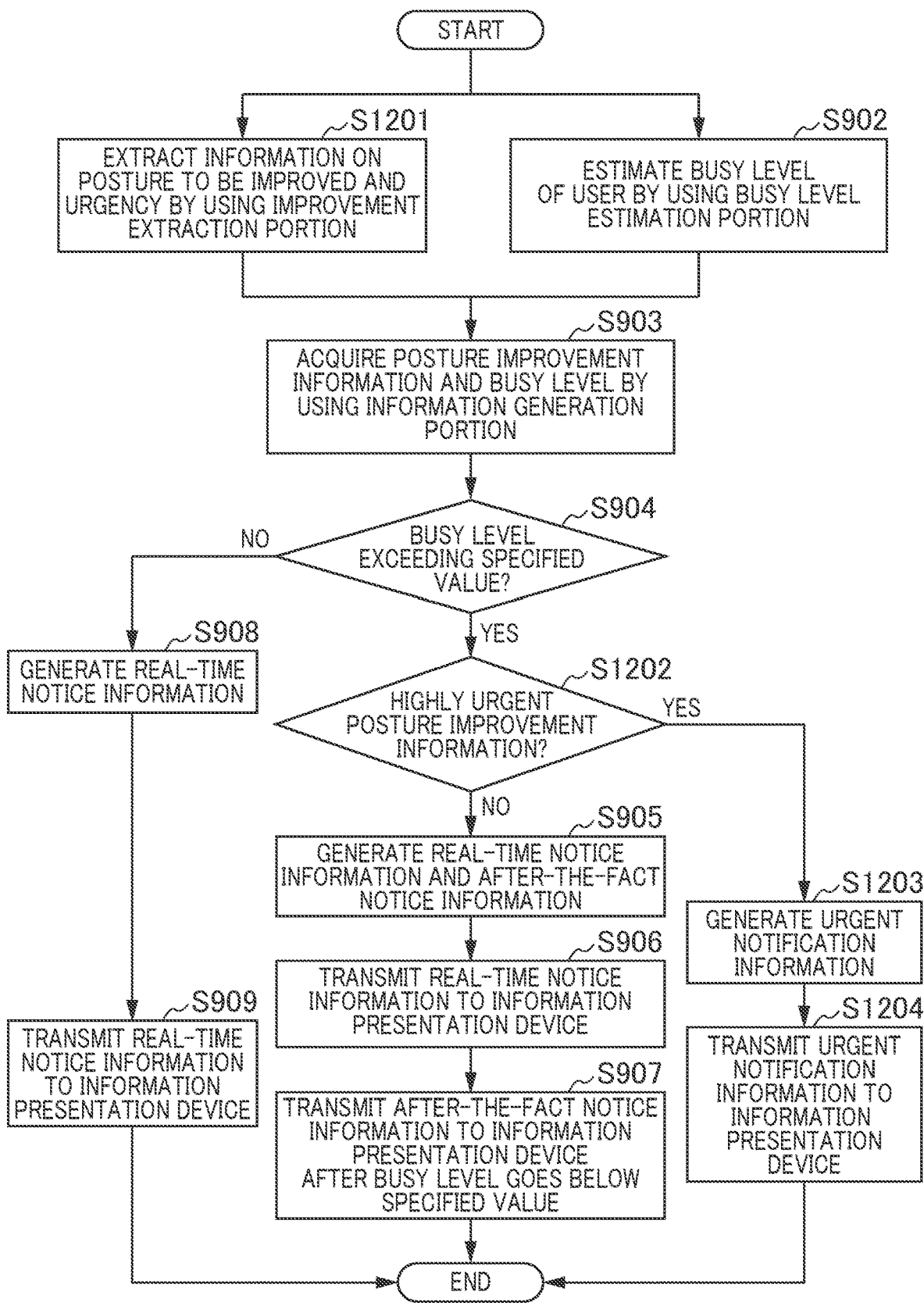
FIG. 14 is a diagram illustrating a flow of the motion evaluation method according to the present embodiment.

FIG. 14 is a flowchart illustrating one technique to allow the workload estimation portion 112 to extract an urgency concurrently with an improvement and transmit urgent notification information according to the urgency.

In this case, at S1201, the improvement extraction portion 113 extracts the posture improvement information and the urgency. The urgency can use a criterion as to whether the estimated physical load exceeds a specified value (particularly, whether the physical load is extremely high), for example.

At S1202, the information generation portion 115 determines whether the urgency is high in the situation where the busy level exceeds the specified value. If the urgency is high (S1202: YES), the information generation portion 115 extracts to generate the urgent notification information from the presentation information table 127 at S1203 and transmits the urgent notification information to the information display device 200 at S1204.

The urgent notification information may be given a predetermined emphasis process to attract the user's attention more than the real-time notice information.

Specific examples may include a warning tone louder than the sound specified in the real-time notice information, a distinguishing warning tone characterized by the timbre or melody pattern greatly differing from that of the real-time notice information, and eye-catching video information such as strong vibrations, flashy colors, or blinking patterns. When the physical load on the user is abnormally high and there is a risk of injury, it is possible to prevent the injury, for example, by presenting the information even if the busy level exceeds a specified value.

FIFTH EMBODIMENT

The first and second embodiments do not change the information generated from the information generation portion 115 even if the workload estimation portion 112 repeatedly extracts similar improvements. As another example to be described below, the information generation portion 115 compares the improvement with the previous notification time when the workload estimation portion 112 repeatedly finds the same improvement. Within a given period, the information generation portion 115 cancels the presentation of the real-time notice information.

Figure 15:
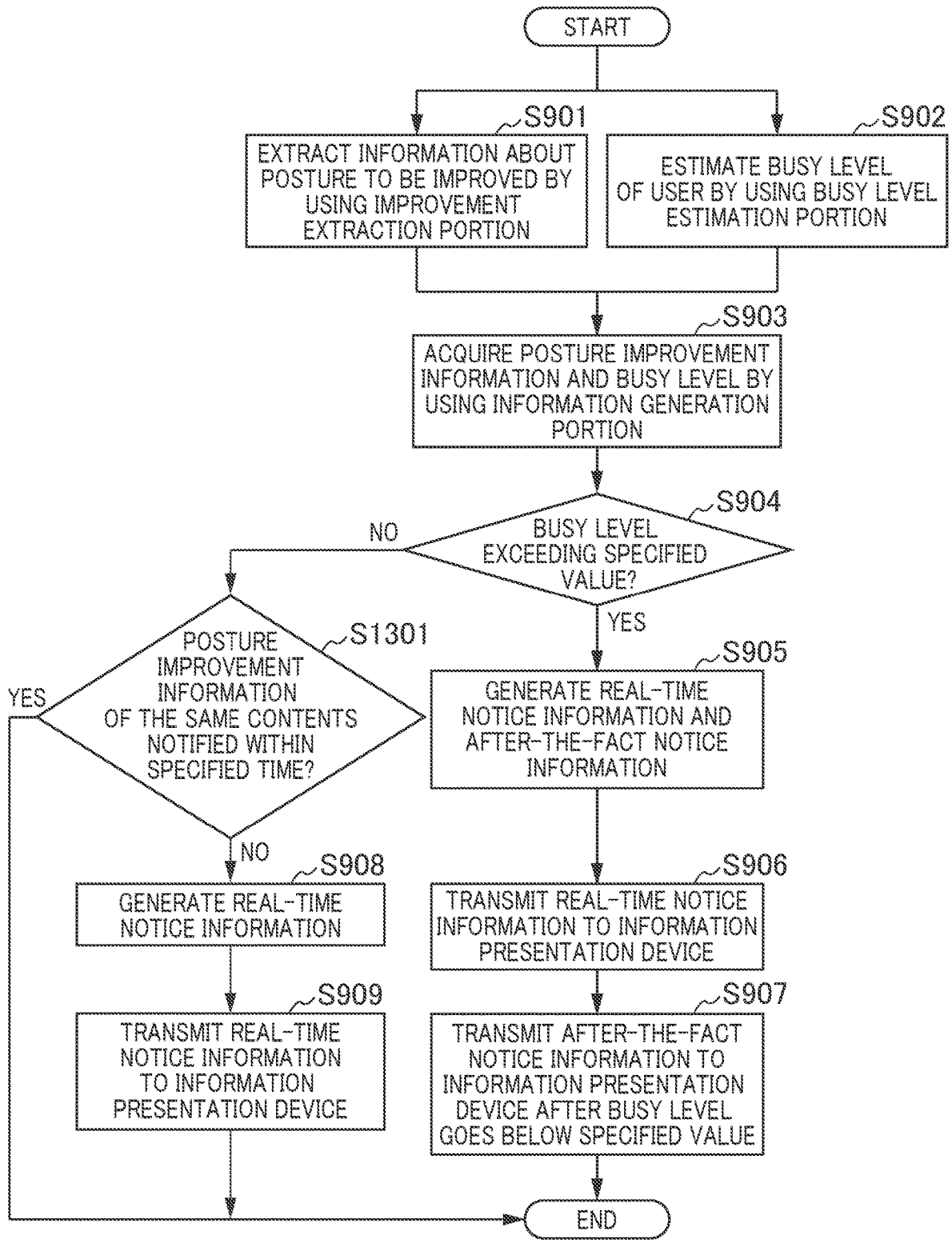
FIG. 15 is a diagram illustrating a flow of the motion evaluation method according to the present embodiment.
Figure 16:
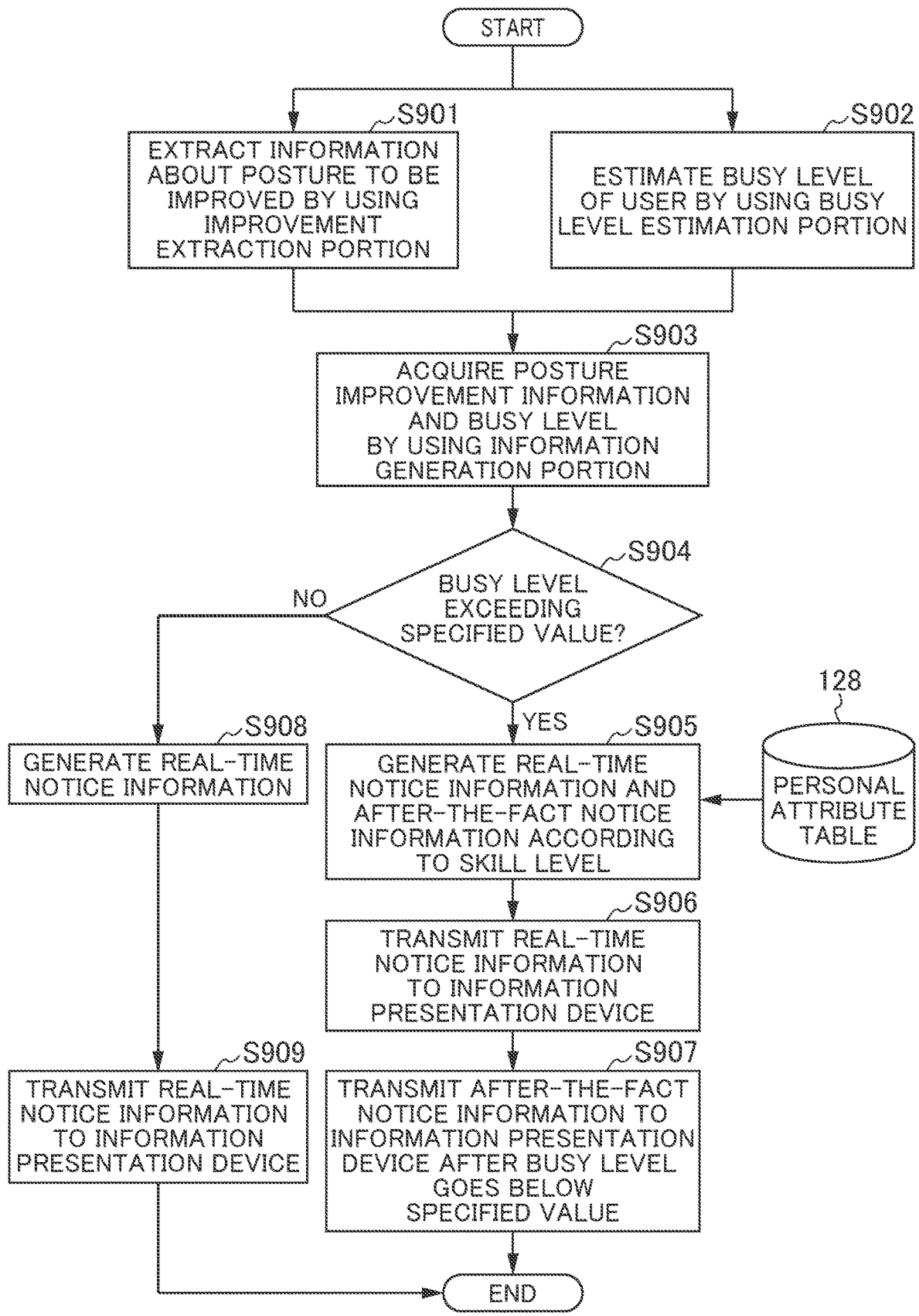
FIG. 16 is a diagram illustrating a flow of the motion evaluation method according to the present embodiment.

FIG. 15 is a flowchart illustrating a technique of changing the content of the generated work improvement proposal information 50 according to the number of repeatedly occurring similar improvements.

The processes up to S904 in the flowchart are equal to those in the flowchart in FIG. 10. The description below explains S1301 and later.

At S1301, the information generation portion 115 determines whether the posture improvement information having the same content is notified to a predetermined user within a specified period.

If the notification is given within a specified period (S1301: YES), the information generation portion 115 cancels the presentation of the same information. Even if the user repeats the same incorrect posture, it is possible to avoid attracting the user's attention more than necessary because the same real-time notice information is repeatedly presented to the user. The information useful for improving postures can be presented.

SIXTH EMBODIMENT

The first embodiment presents the same information to all users under the condition of the same posture improvement information and the same busy level. The description below explains another example of changing the information presented to the user based on personal attributes such as age, gender, skill, and skill level of the user, for example.

FIG. 15 is a flowchart illustrating a technique of generating notification information according to the user's skill level. The technique uses "skill level" concerning a given work as a personal attribute, for example. However, other personal attributes may be used.

The information generation portion 115 references the user's skill level in the personal attribute table 128 (see FIG. 17) when generating notification information at S905. If the user's skill level is lower than the standard, the information generation portion 115 extracts, for example, notification information (such as C or lower as the value in the skill level column) to be carefully explained from the basic concept of the work from the presentation information table 127. Similarly, if the user's skill level is higher than the standard, the information generation portion 115 may omit the explanation of basic concepts, for example, and generate simple notification information (such as A+ or higher as the value in the skill level column) extracted from the presentation information table 127.

The user's skill level is determined based on a method such as using skill levels created from the history of presentations of the posture improvement information in past works or performing a simple test before performing the work. These are just examples and the means for grasping the skill levels are not limited thereto.

The learning effect can be enhanced by changing the contents of the information presented to the user according to the user's attributes such as skill levels and providing more careful and detailed information to low-skilled users.

SEVENTH EMBODIMENT

According to the first embodiment, the method of estimating the busy level of the user uses the user's work content as a reference. As another example, it is also possible to estimate the busy level through the use of information from the user's work process, instruments targeted at the work, and sensors such as cameras, microphones, and thermometers installed in the environment where the user is working.

In this case, the busy level estimation portion 114 acquires information (such as data resulting from observing the operating states of the instruments and noise levels in the work environment) on at least one of the events such as the user's work process, the operating state of the device targeted at the work, and the work environment from the above-mentioned sensors as means to monitor the events. The busy level estimation portion 114 checks the information about the event and the motion data 40 against the information about the user's busy level to specify the user's busy level.

As a possible mode, the busy level estimation portion 114 checks each value of the rotation speed of the operating instrument and the noise level of the working environment against the reference value specified for the event in the busy level evaluation table 126, for example. The busy level estimation portion 114 then specifies the busy level associated with the corresponding reference value as the busy level of the user.

In this case, the busy level evaluation table 126 differs from that illustrated in FIG. 9. The information processing device 100 previously stores the busy level evaluation table 126 that specifies busy levels corresponding to ranges of values for events (such as noise at level bb or an operating value ranging from cc to dd) based on various types of events (such as operating values, sound, or temperature of the instrument) concerning the environment as keys.

The above-described information on environment-related events may apply to information entered by the user from a mobile terminal carried by the user, for example.

The busy level of the user can be accurately determined by also taking into account information such as the operating speed of the instrument targeted at the work or the resulting noise level in the surrounding environment, for example. Consequently, this can more accurately specify improvement suggestion information and output it to the user. Further, it is possible to more efficiently transmit appropriate information on the motion improvement to a person in motion.

The information generation portion 115 may control the form of the improvement suggestion information transmitted to the information presentation device 200 based on the above-mentioned information on the environmental events.

Based on the above-mentioned information about the environmental events, the information generation portion 115 extracts the improvement suggestion information in a predetermined form according to the work environment from the presentation information table 127. Alternatively, the information generation portion 115 processes the improvement suggestion information into a predetermined form and outputs it to the information presentation device 200.

The following operation is available. For example, the information generation portion 115 acquires a value for the noise level in the work environment from the microphone as a sensor installed in the work environment. If the value is greater than a predetermined criterion, the information generation portion 115 extracts non-voice notification information from the presentation information table 127 during the information presentation and transmits the notification information to the information presentation device 200.

In an environment where the noise level exceeds the criterion, the improvement suggestion information is output in the form of oscillation by a vibrator or blinking by a lighting lamp. In an environment where the noise level is below the criterion but the illuminance is below the criterion, the improvement suggestion information is output in the form of specific sound output or oscillation by a vibrator. The information can be transmitted in versatile and accurate forms adaptable to the environment. As a result, it is possible to more efficiently transmit appropriate information on the motion improvement to a person in motion. It is possible to comprehend the user's states from multiple viewpoints and present the information according to the user's states.

While there have been described specific preferred embodiments of the present invention, it is to be distinctly understood that the invention is not limited thereto but may be otherwise variously embodied within the spirit and scope of the invention.

The present embodiment can efficiently transmit appropriate information on the motion improvement to a person in motion.

The description of the present specification clarifies at least the following. In the motion evaluation system according to the present embodiment, when the busy level is higher than or equal to a specified criterion, the arithmetic device may perform the output of predetermined real-time notice information within a predetermined time from an occurrence of a motion concerning the improvement as the improvement suggestion information corresponding to the first one of the multiple times. When the busy level falls below the specified criterion after the presentation, the arithmetic device may perform the output of predetermined after-the-fact notice information.

As a result, the following control is available. A person in a busy state, for example, at work, is presented with short and clear improvement suggestion information, or information just indicating that the person is targeted at suggestions for the improvement. When the busy state is resolved, detailed and specific improvement suggestion information is presented. It is further possible to more efficiently transmit appropriate information on the motion improvement to a person in motion.

In the motion evaluation system according to the present embodiment, when the same improvement is repeatedly specified for the user within a specified time, the arithmetic device may perform a predetermined emphasis process on the improvement suggestion information and perform the output of the improvement suggestion information treated with the emphasis process.

It is possible to make the user strongly aware of a motion that needs improvement. It is further possible to more efficiently transmit appropriate information on the motion improvement to a person in motion.

In the motion evaluation system according to the present embodiment, the arithmetic device may determine a state of the motion and, when the urgency of the improvement for a motion targeted at the improvement exceeds a specified criterion, perform the output of the improvement suggestion information treated with a predetermined emphasis process within a predetermined time from an occurrence of the motion targeted at the improvement, regardless of degrees of the busy level.

When an improper motion reaches a level that can lead to the occurrence of a serious incident, it is possible to make the user surely recognize the situation and struggle for improvements. It is further possible to more efficiently transmit appropriate information on the motion improvement to a person in motion.

In the motion evaluation system according to the present embodiment, the arithmetic device may repeatedly specify the same improvement regarding the user within a specified time and decrease the repetition of output performed on improvement suggestion of the same contents within a specified time.

There may be a case of repeatedly outputting the improvement suggestion information with the same content concerning an improvement that is not particularly urgent. In such a case, it is possible to avoid a situation where the user recognizing the information is unnecessarily confused. It is further possible to more efficiently transmit appropriate information on the motion improvement to a person in motion.

In the motion evaluation system according to the present embodiment, the storage device may further store information about personal attributes of the user. The arithmetic device may extract the improvement suggestion information while referencing information about the personal attribute of the user in the storage device. The arithmetic device may extract the improvement suggestion information corresponding to the personal attribute from the storage device. The arithmetic device may output the improvement suggestion information to the information presentation device.

It is possible to flexibly control the improvement suggestion information according to attributes such as user's age, gender, skill, and skill level and transmit the improvement suggestion information as information easily recognizable for the user. It is further possible to more efficiently transmit appropriate information on the motion improvement to a person in motion.

In the motion evaluation system according to the present embodiment, the arithmetic device may reference information about a skill level of the motion of the user as information about the personal attribute, extract the improvement suggestion information corresponding to the skill level from the storage device, and output the improvement suggestion information to the information presentation device.

It is possible to present appropriate information (information devoid of waste or information including the basic knowledge for beginners) as the improvement suggestion information for the user based on the knowledge background according to the skill level. It is further possible to more efficiently transmit appropriate information on the motion improvement to a person in motion.

In the motion evaluation system according to the present embodiment, when specifying the busy level, the arithmetic device may acquire information on at least one of the user's work process, the operating status of the work target device, and each event in the work environment from the sensor as a monitoring solution for the event in addition to the motion data, check the information about the event and the motion data against information about busy levels of a user in the reference information, and specify a busy level of the user.

The busy level of the user can be determined accurately by also taking into account information such as the operating speed of the instrument targeted at the work or the resulting noise level in the surrounding environment, for example. Consequently, this can more accurately specify the improvement suggestion information and output it to the user. It is further possible to more efficiently transmit appropriate information on the motion improvement to a person in motion.

In the motion evaluation system according to the present embodiment, when outputting the improvement suggestion information to the information presentation device, the arithmetic device may extract improvement suggestion information in a predetermined form according to the working environment from the storage device based on information about the working environment or process the improvement suggestion information into the form to output the improvement suggestion information to the information presentation device.

In an environment where the noise level exceeds the criterion, the improvement suggestion information is output in the form of oscillation by a vibrator or blinking by a lighting lamp. In an environment where the noise level is below the criterion but the illuminance is below the criterion, the improvement suggestion information is output in the form of specific sound output or oscillation by a vibrator. The information can be transmitted in versatile and accurate forms adaptable to the environment. It is further possible to more efficiently transmit appropriate information on the motion improvement to a person in motion.

In the motion evaluation system according to the present embodiment, when no improvement is specified, the arithmetic device may output information appreciating the correctness of a motion of the user to the information presentation device.

It is possible to increase the motivation of the user to work, for example. This can also keep the attention to the output of the improvement suggestion information while appropriately maintaining the motivation of the user to work, for example. It is further possible to more efficiently transmit appropriate information on the motion improvement to a person in motion.

What is claimed is:

1. A motion evaluation system comprising:
an information processing device,
wherein the information processing device includes:
a communication device that communicates with a sensor to observe a motion of a user;
a storage device that stores reference information defining various states of the motion and various information suggesting improvement of the motion; and
an arithmetic device that performs a process to acquire motion data acquired by observing the user through the use of the sensor via the communication device, checks the motion data against information about the correctness of motions in the reference information to determine a state of motion of the user and specify, as an improvement, a motion in a state to be improved among the motions, a process to check the motion data after the motion corresponding to the improvement against information about busy levels of the user among the reference information to specify a busy level of the user, and a process to extract, as improvement suggestion information about the improvement, information with different contents at each of a plurality of times from the storage device based on the improvement and a rule predetermined according to each situation of the busy level and output the information to an information presentation device for the user.

2. The motion evaluation system according to claim 1, wherein, when the busy level is higher than or equal to a specified criterion, the arithmetic device performs the output of predetermined real-time notice information within a predetermined time from an occurrence of a motion concerning the improvement as the improvement suggestion information corresponding to the first one of the plurality of times and, when the busy level falls below the specified criterion after the presentation, performs the output of predetermined after-the-fact notice information.

3. The motion evaluation system according to claim 1, wherein, when the same improvement is repeatedly specified for the user within a specified time, the arithmetic device performs a predetermined emphasis process on the improvement suggestion information and performs the output of the improvement suggestion information treated with the emphasis process.

4. The motion evaluation system according to claim 1, wherein the arithmetic device determines a state of the motion and, when the urgency of improvement for a motion targeted at the improvement exceeds a specified criterion, perform the output of the improvement suggestion information treated with a predetermined emphasis process within a predetermined time from an occurrence of the motion targeted at the improvement, regardless of degrees of the busy level.

5. The motion evaluation system according to claim 1, wherein the arithmetic device repeatedly specifies the same improvement regarding the user within a specified time and decreases the repetition of output performed on improvement suggestion of the same contents within a specified time.

6. The motion evaluation system according to claim 1, wherein the storage device further stores information about personal attributes of the user; and
wherein the arithmetic device extracts the improvement suggestion information while referencing information about the personal attribute of the user in the storage device, extracts the improvement suggestion information corresponding to the personal attribute from the storage device, and outputs the improvement suggestion information to the information presentation device.

7. The motion evaluation system according to claim 6, wherein the arithmetic device references information about a skill level of the motion of the user as information about the personal attribute, extracts the improvement suggestion information corresponding to the skill level from the storage device, and outputs the improvement suggestion information to the information presentation device.

8. The motion evaluation system according to claim 1, wherein, when specifying the busy level, the arithmetic device acquires information on at least one of a work process, an operating status of the work target device, and each event in the work environment of the user from the sensor as a monitoring solution for the event in addition to the motion data, checks the information about the event and the motion data against information about busy levels of the user in the reference information, and specifies a busy level of the user.

9. The motion evaluation system according to claim 8, wherein, when outputting the improvement suggestion information to the information presentation device, the arithmetic device extracts improvement suggestion information in a predetermined form according to the working environment from the storage device based on information about the working environment or processes the improvement suggestion information into the form to output the improvement suggestion information to the information presentation device.

10. The motion evaluation system according to claim 1, wherein, when no improvement is specified, the arithmetic device outputs information appreciating the correctness of a motion of the user to the information presentation device.

11. A motion evaluation device comprising:
a communication device that communicates with a sensor to observe a motion of a user;
a storage device that stores reference information defining various states of the motion and various information suggesting improvement of the motion; and
an arithmetic device that performs a process to acquire motion data acquired by observing the user through the use of the sensor via the communication device, check the motion data against information about the correctness of motions in the reference information to determine a state of motion of the user and specify, as an improvement, a motion in a state to be improved among the motions, a process to check the motion data after the motion corresponding to the improvement against information about busy levels of the user among the reference information to specify a busy level of the user, and a process to extract, as improvement suggestion information about the improvement, information with different contents at each of a plurality of times from the storage device based on the improvement and a rule predetermined according to each situation of the busy level and output the information to an information presentation device for the user.

12. A motion evaluation method implemented by an information processing device including a communication device that communicates with a sensor to observe a motion of a user and a storage device that stores reference information defining various states of the motion and various information suggesting improvement of the motion, comprising:

performing a process to acquire motion data acquired by observing the user through the use of the sensor via the communication device, check the motion data against information about the correctness of motions in the reference information to determine a state of motion of the user, and specify, as an improvement, a motion in a state to be improved among the motions, a process to check the motion data after the motion corresponding to the improvement against information about busy levels of the user among the reference information to specify a busy level of the user, and a process to extract, as improvement suggestion information about the improvement, information with different contents at each of a plurality of times from the storage device based on the improvement and a rule predetermined according to each situation of the busy level and output the information to an information presentation device for the user.

* * * * *